(12) United States Patent
Ciarrocca

(10) Patent No.: US 6,773,434 B2
(45) Date of Patent: Aug. 10, 2004

(54) COMBINATION BIPOLAR FORCEPS AND SCISSORS INSTRUMENT

(75) Inventor: Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 121 days.

(21) Appl. No.: 10/219,571

(22) Filed: Aug. 15, 2002

(65) Prior Publication Data
US 2003/0055424 A1 Mar. 20, 2003

Related U.S. Application Data

(60) Provisional application No. 60/323,156, filed on Sep. 18, 2001.

(51) Int. Cl.[7] ............................................... A61B 18/14
(52) U.S. Cl. ........................ 606/51; 606/52; 606/170; 606/174; 606/205; 606/207
(58) Field of Search ........................... 606/51, 52, 170, 606/174, 205, 207

(56) References Cited

U.S. PATENT DOCUMENTS

| 4,655,216 A | 4/1987 | Tischer |
| 5,342,381 A | 8/1994 | Tidemand |
| 5,403,312 A | 4/1995 | Yates et al. |
| 5,445,638 A | 8/1995 | Rydell et al. |
| 5,456,684 A | 10/1995 | Schmidt et al. |
| 5,458,598 A | 10/1995 | Feinberg et al. |
| 5,462,546 A | 10/1995 | Rydell |
| 5,573,535 A | 11/1996 | Viklund |
| 5,665,100 A | 9/1997 | Yoon |
| 5,697,949 A | 12/1997 | Giurtino et al. |
| 5,797,941 A * | 8/1998 | Schulze et al. ............. 606/171 |
| 5,922,001 A | 7/1999 | Yoon |
| 5,964,758 A | 10/1999 | Dresden |
| 5,984,938 A | 11/1999 | Yoon |
| 6,208,877 B1 | 3/2001 | Henry, Jr. |
| 6,267,761 B1 | 7/2001 | Ryan |
| 6,270,497 B1 | 8/2001 | Sekino et al. |
| 2002/0111624 A1 * | 8/2002 | Witt et al. ..................... 606/51 |

FOREIGN PATENT DOCUMENTS

| EP | 0 878 169 A1 | 11/1998 |
| WO | WO 99/66850 A1 | 12/1999 |
| WO | WO 01/54604 A1 | 8/2001 |

* cited by examiner

Primary Examiner—Lee S. Cohen

(57) ABSTRACT

A surgical instrument is provided having a shaft with a handpiece at a proximal end and a grasping device at the distal end. The grasping device has a first jaw element and a second jaw element pivotably coupled thereto and selectively pivotable between open and closed positions. The instrument also includes a cutting device having a first cutting element and a second cutting element pivotably coupled to the first cutting element. The cutting device is movable between a retracted position wherein it is positioned within the shaft and an extended position wherein it is disposed at the distal end of the shaft. When in the extended position, the cutting elements are coupled to the respective jaw elements for movement therewith between open and closed positions. Also provided is a method for surgically manipulating tissue using such a device.

22 Claims, 15 Drawing Sheets

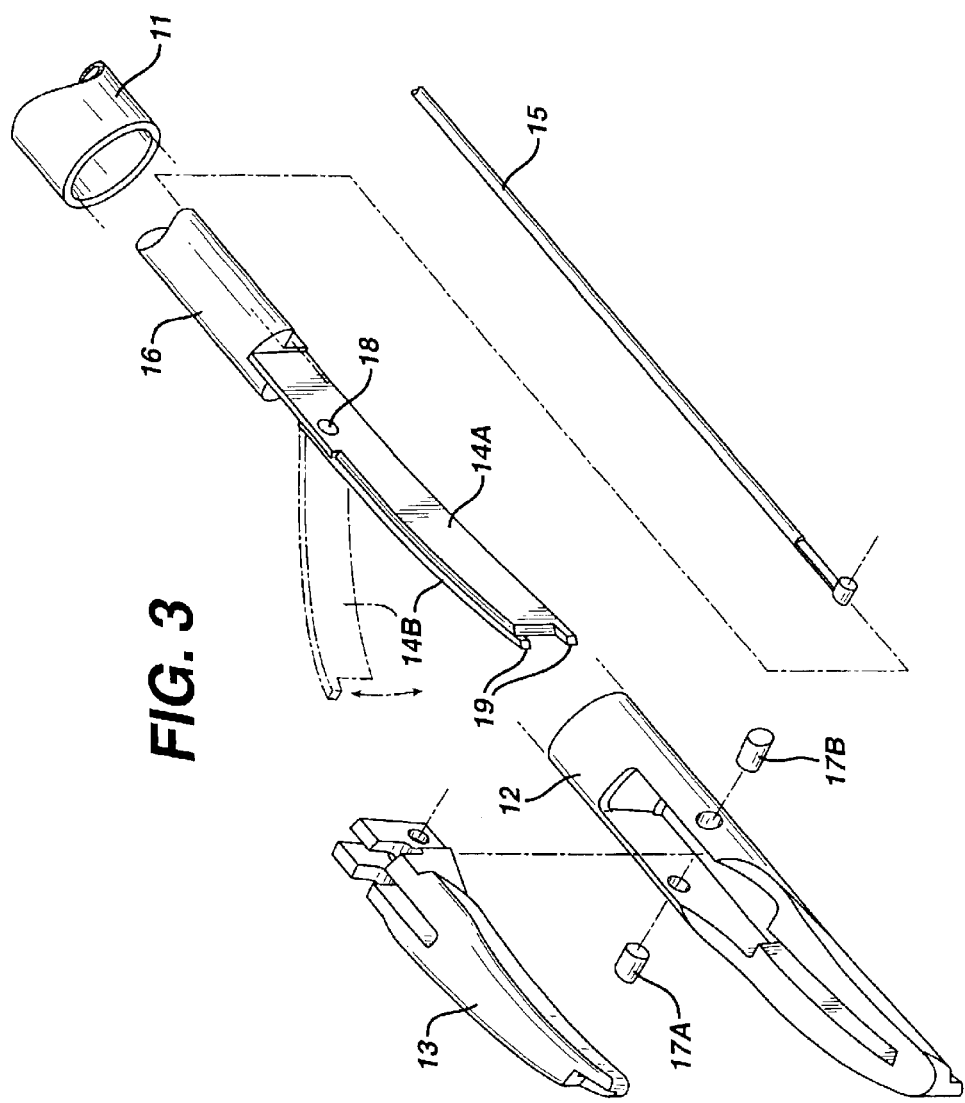

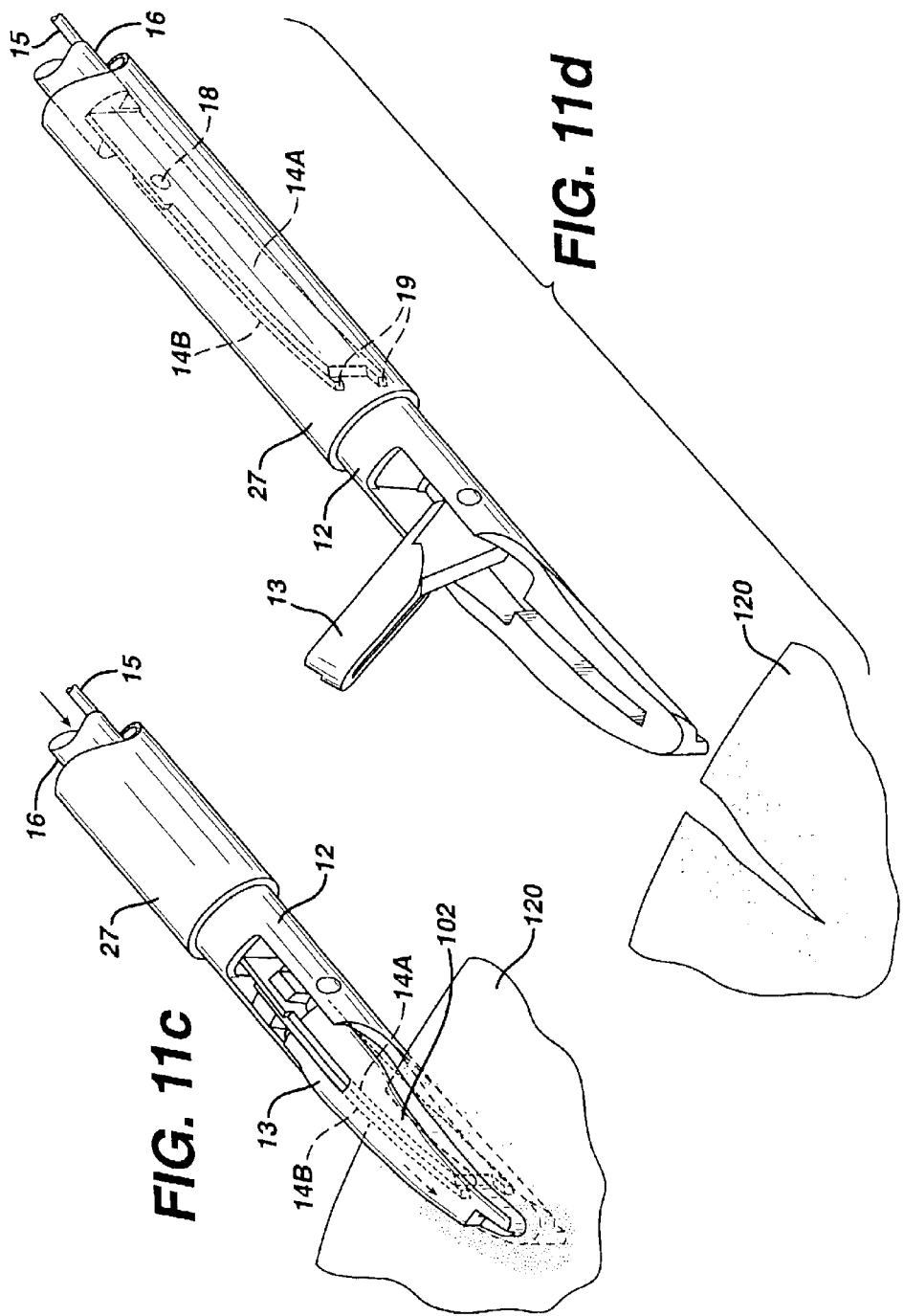

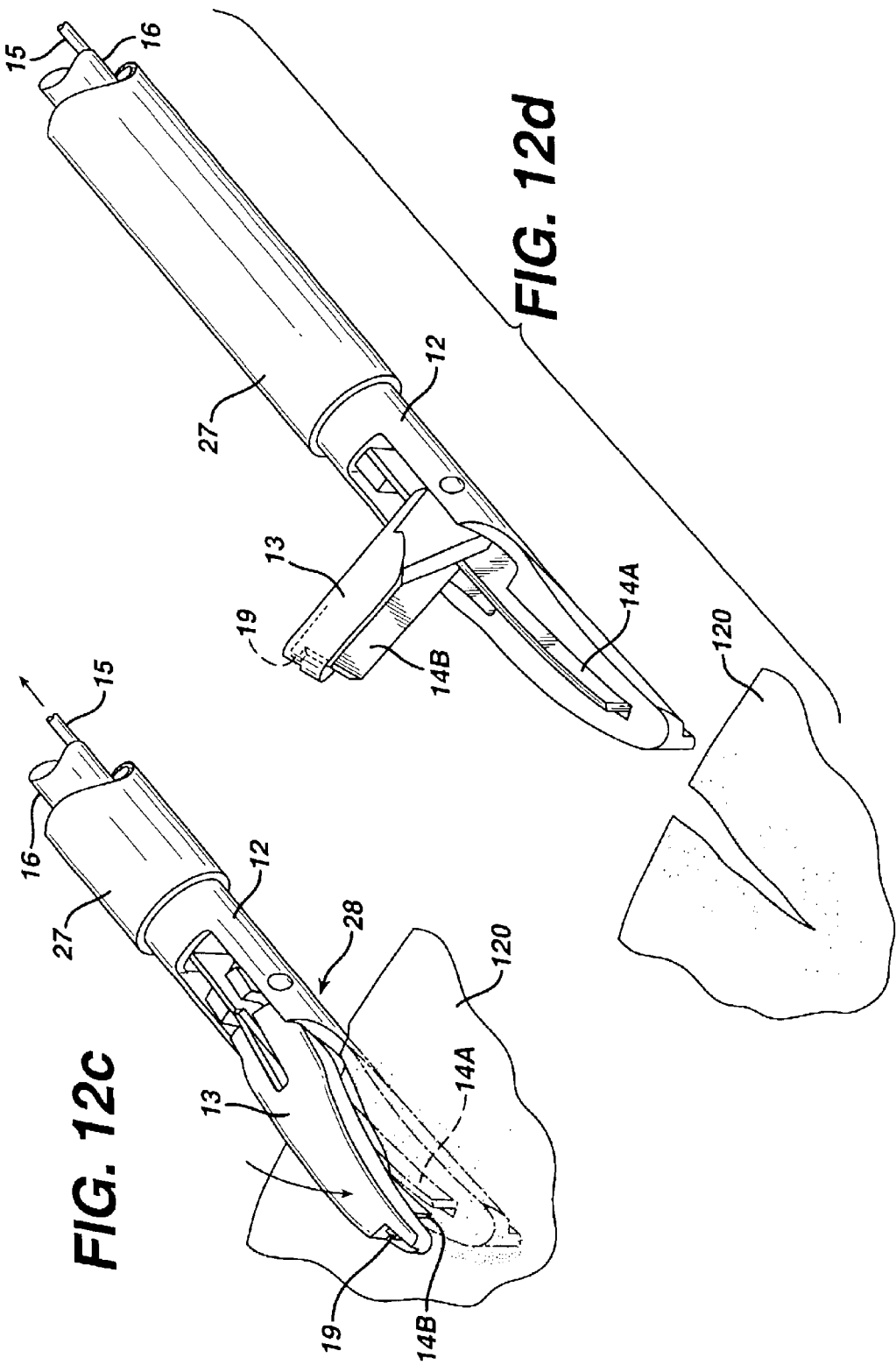

COMBINATION BIPOLAR FORCEPS AND SCISSORS INSTRUMENT

CROSS-REFERENCE TO RELATED APPLICATION

This application claims priority of Provisional application Serial No. 60/323,156, filed Sep. 18, 2001.

BACKGROUND OF THE INVENTION

1. Field of the Invention

This invention relates generally to surgical forceps and scissors, and in particular, to a combination bipolar forceps and scissors surgical instrument.

2. Description of the Background Art

The utility of a surgical implement for performing both tissue cutting and coagulation has been identified and addressed previously by a number of designs. U.S. Pat. Nos. 4,655,216, 5,445,638, 5,458,598, and 5,573,535 all describe bipolar coagulating instruments with separately actuable single-blade cutting mechanisms. The single cutting blades featured in these designs lack precision due to the tendency of the blade to displace tissue from the grasper jaws while cutting tissue. Further, these designs expose sharpened portions of the cutting blade to tissue outside the grasper jaws, which creates the risk of inadvertent cutting of tissue and structures surrounding the intended treatment sight. Durability and longevity of the cutting blade can also be an issue with this cutting mechanism since it relies greatly on the sharpness of the delicate cutting edge. Further, the single-blade cutting mechanism suffers when compared to a conventional surgical scissors in terms of functionality.

Previous attempts at constructing combination bipolar forceps and scissors devices involved either segmenting the grasper jaws into a distal grasping and coagulating portion and a proximal shearing scissors portion, or employing two independent mechanisms for the graspers and scissors. The former approach, which is described in U.S. Pat. Nos. 5,342,381, 5,462,546, and 6,206,877 results in a device with relatively small grasping and coagulating surfaces and scissors mechanisms. This limits the area and thickness of tissue that can be coagulated and/or transected by the device. Further, because the scissor blades are fixed in place, it is possible to unintentionally cut tissue that has not been coagulated if great care is not taken when grasping tissue with the distal forceps portion of the jaw.

Designs featuring independent grasping and scissor mechanisms as described in U.S. Pat. No. 5,964,758 are mechanically complex. The scissor mechanisms are either permanently installed, which limits their utility as an a traumatic grasper or coagulating forceps, or controlled by a separate mechanism that further complicates their application.

Further, no forceps and scissor combinations previously described takes advantage of an offset electrode arrangement which greatly reduces the area of tissue coagulated during application of bipolar energy, and results in significantly reduced levels of undesirable collateral tissue damage. In conventional prior-art bipolar forceps, current 6 from the electrosurgical generator is passed between jaws 4 and 5 through tissue 7 captured between the jaws, as shown in FIGS. 1a and 1b. The arrangement of the electrodes in this opposing fashion causes some of the electrosurgical current 8 flowing between the jaws to pass through tissue outside of the jaws, thus causing collateral tissue destruction. Offset electrode technology is disclosed in U.S. Pat. No. 5,403,312, which is incorporated herein by reference.

U.S. Pat. No. 5,984,938 describes a forcep concept with deployable scissor inserts; however, this design describes a conventional mechanical grasper with sprung jaws, not a bipolar coagulating forcep with a hinged jaw. Further, the inserts described do not possess a sharpened leading edge, which would allow them to be used as tissue transectors.

Finally, the straight and un-tapered form of the jaws described in all of the previous disclosures limits user visibility of the distal tip, compromises their ability to access recessed structures, and prevents them from effectively being used as a mechanical dissector.

Thus, there is a need for an improved combination bipolar forceps and scissor device that overcomes deficiencies of prior art devices.

SUMMARY OF THE INVENTION

A surgical instrument is provided including a shaft having a proximal end and a distal end, a handpiece disposed at the proximal end of the shaft, and a grasping device disposed at the distal end of the shaft, and having a first jaw element and a second jaw element pivotally coupled to the first jaw element and selectively pivotable relative to the first jaw element between an open position and a closed position. The instrument also includes a cutting device having a first cutting element and a second cutting element pivotally coupled to the first cutting element. The cutting device is movable between a retracted position wherein it is positioned within the shaft and a extended position wherein it is disposed at the distal end of the shaft. When the cutting device is in the extended position, the first and second cutting elements are coupled to the first and second jaw elements respectively for movement therewith between open and closed positions.

In one embodiment the instrument further includes a grasper activation assembly for selectively moving the grasping device between the open and closed positions, and a cutting device activation assembly for selectively moving the cutting device between the retracted and extended positions. In yet another embodiment, the grasping activation assembly further includes a grasping activator element associated with the handpiece, and grasping activation coupling elements for coupling the grasping activator element with the grasping device so that selective movement of the grasping device between the open and closed positions can be accomplished by manipulating the grasping activator element. The cutting activation assembly also further comprises a cutting activator element associated with the handpiece, and cutting activator coupling elements for coupling the cutting activation element with the cutting device so that selective movement of the cutting device between the retracted and extended positions can be accomplished by manipulating the cutting activator element. In yet another embodiment, the grasping activation coupling elements include an elongate element positioned within the shaft, wherein longitudinal movement of the elongate element along the axis of the shaft causes the second jaw element to pivot relative to the first jaw element between the open and closed positions. Further, the cutting activation elements include an elongate element positioned within the shaft, wherein longitudinal movement of the elongate element along the axis of the shaft causes the cutting device to move between the retracted and extended positions.

In alternate embodiments, the instrument further includes at least one pair of bipolar electrodes contained within the first and second jaw elements respectively, the arrangement being such that when the grasping device is in the closed position, the electrodes are substantially facing towards one another and either substantially offset from one another or substantially opposing one another.

In yet another embodiment, the first and second jaw elements have first and second channels therein respectively.

When in the extended position, the first and second cutting elements are positioned within the first and second channels respectively. In yet another embodiment, the instrument further includes means for impeding rotation of the grasping element when in the closed position. In an alternate embodiment, the first and second cutting elements have first and second protrusions respectively that, when the cutting device is in the extended position, are received within first and second recesses in the first and second grasping elements respectively.

Also provided is a surgical instrument including a shaft having a proximal end and a distal end, a handpiece disposed at the proximal end of the shaft, and a grasping device disposed at the distal end of the shaft having first and second jaw elements pivotally coupled to one another and pivotable relative to one another between opened position and a closed positions. The instrument further includes a cutting device having a first cutting element and a second cutting element pivotally coupled to the first cutting element. The cutting device is movable between a retracted position wherein it is positioned within the shaft and a extended position wherein it is disposed at the distal end of the shaft. When the cutting device is in the extended position, the first and second cutting elements are coupled to the first and second jaw elements respectively for movement therewith between open and closed positions, and at least one of said first and second cutting elements has a sharpened leading edge capable of dissecting tissue when the cutting device is moved from the retracted position to the extended position.

A method for surgically manipulating tissue is also provided including the steps of grasping a portion of tissue using a grasping device positioned at a distal end of a shaft of a surgical instrument, coagulating the grasped tissue by applying bipolar electrical energy to bipolar electrodes within the grasping device, and cutting the tissue by deploying a cutting device from a first position wherein it is retracted within the shaft of the surgical instrument, to a second position wherein it extends into the grasping device.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 3 is an exploded perspective view of the distal end of one embodiment of the present invention;

FIGS. 11a–11d illustrate one method of operation of an embodiment of the present invention;

FIGS. 12a–12d illustrate an alternate method of operation of an embodiment of the present invention.

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Bipolar electrosurgical tools are widely used in both open and endoscopic surgery for cutting, vaporizing, and coagulation tissue. The present disclosure provides a surgical instrument that can perform several functions required during laparoscopic surgery. Beyond the creation and maintenance of hemostasis, there are a variety of mechanical functions, including tissue grasping, tissue dissecting, mechanical spreading, and tissue cutting which are desirable. The design of the present invention provides these functions in a single instrument.

Figure 1A:
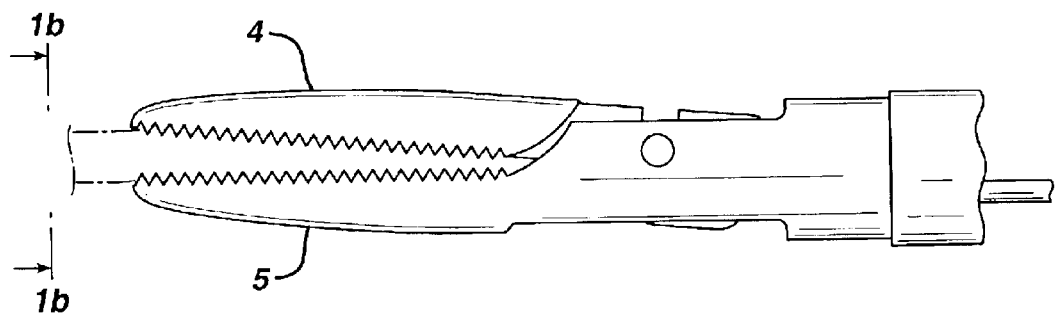
FIG. 1a is a side view of a prior art bipolar grasper.
Figure 1B:
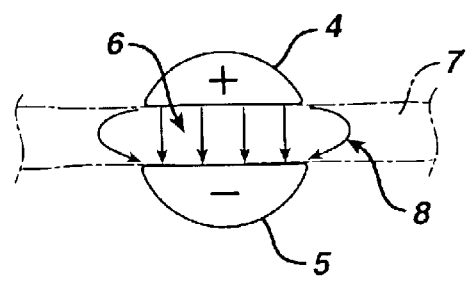
FIG. 1b is an end elevational view as seen along view line 1b—1b of FIG. 1a with arrows indicating current flow between the forceps grasping jaws.
Figure 2A:
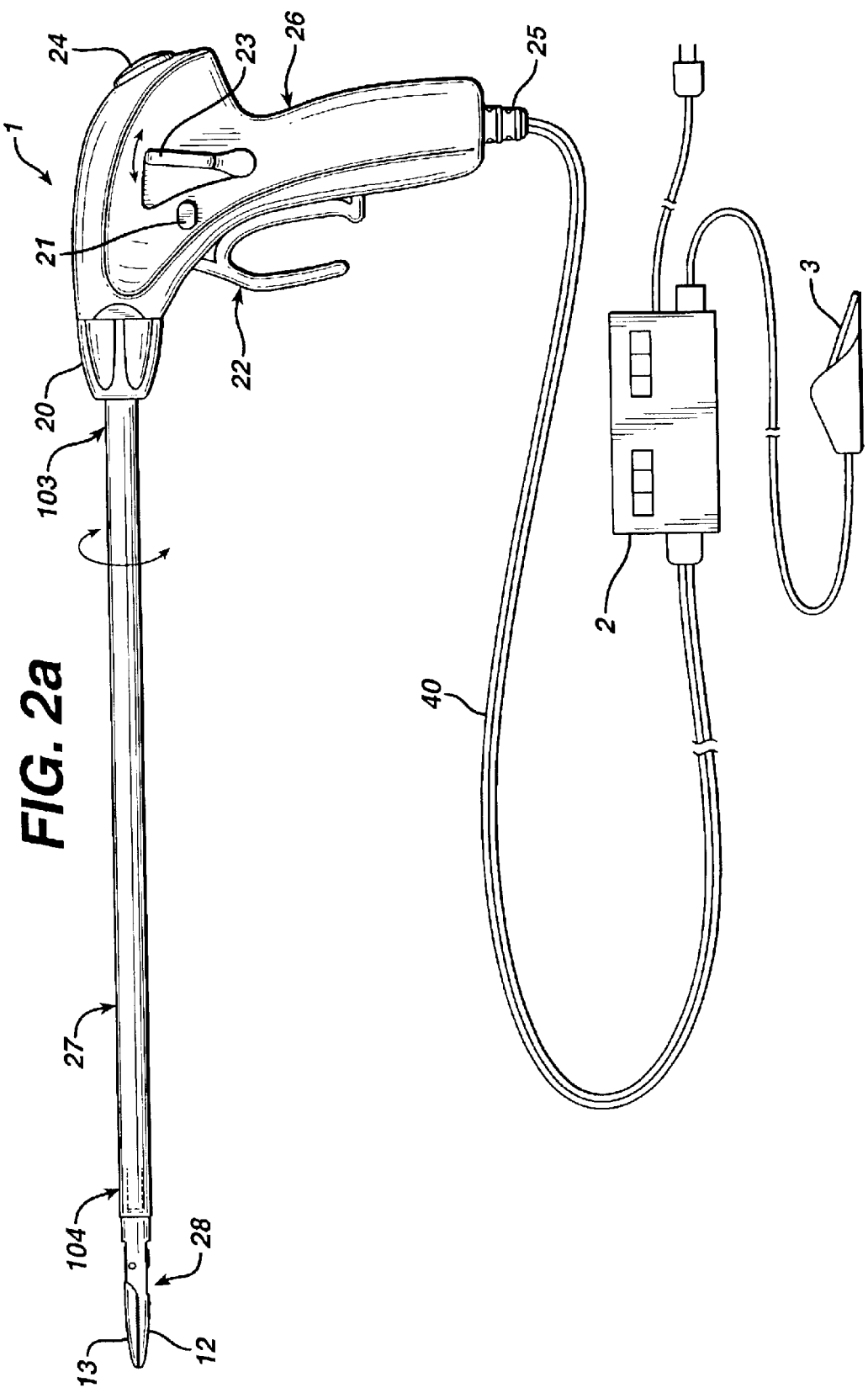
FIG. 2a is a side view of one embodiment of a combination scissors and bipolar forceps surgical instrument according to the present disclosure connected to a bipolar electrosurgical generator.

Referring now to FIG. 2a, a combination bipolar forcep and scissor surgical instrument 1 is shown connected to a common electrosurgical generator 2. Current flow through the bipolar electrodes housed within the jaws of the instrument can be controlled by a foot pedal 3 attached to the generator. Surgical instrument 1 comprises a handle 26, a shaft 27 having a proximal end 103 and a distal end 104 and a lumen extending therethrough, and an end effector such as the illustrated grasping device 28 extending from the distal end of shaft.

Figure 8A:
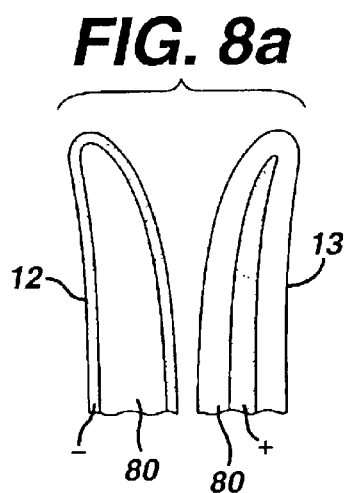
FIGS. 8a–8c are plan views of the grasping faces of the jaws showing various embodiments of the offset electrode arrangement.
Figure 8B:
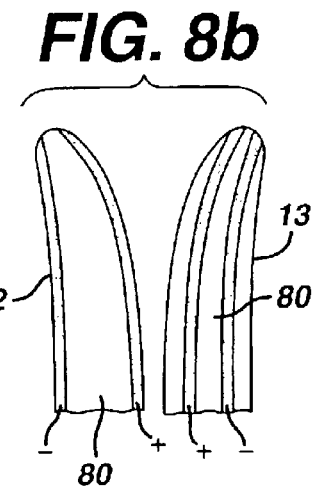
Figure 8C:
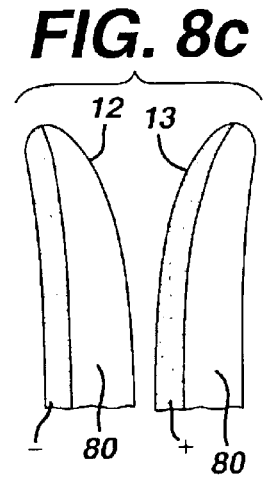
Figure 9A:
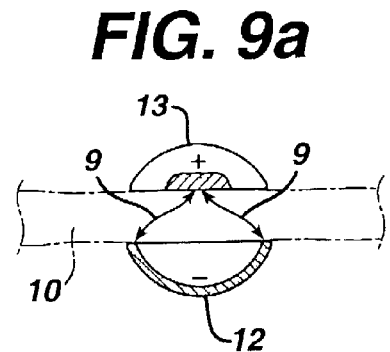
FIGS. 9a–9c are transverse cross-sectional views of the grasper jaws of FIGS. 8a–8c, respectively, further illustrating the offset electrode arrangements.
Figure 9B:
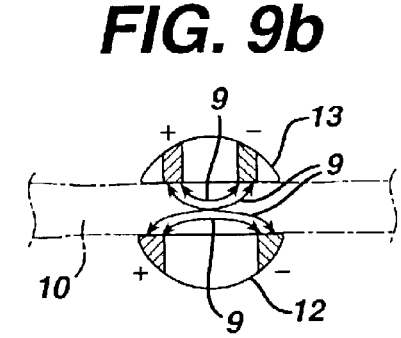
Figure 9C:
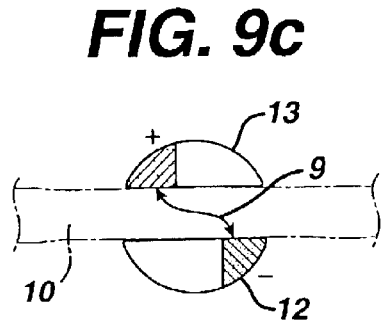

Although numerous arrangements of bipolar electrodes are suitable for use with the present invention, reducing the level of undesirable collateral tissue destruction caused by bipolar forceps is important, and can be accomplished by arranging the electrodes in a fashion that limits the flow of current outside the jaws. In contrast to prior art arrangements such as that shown in FIG. 1b, FIGS. 8a–8c and 9a–9c show possible arrangements of electrodes that accomplish this by offsetting the opposing poles of the electrode pairs. FIGS. 8a–8c are plan views of the grasping faces 80 of jaws 12, 13 of the grasping device 28. FIGS. 9a–9c show a cross-sectional view of these grasping devices respectively. Electricity 9 passing through tissue 10 captured between the jaws 12, 13 stays primarily within the cross section of the jaws, thus limiting collateral thermal injury. FIGS. 6a–6e, illustrate possible grasper jaw forms that are suitable for the present invention. It should be understood, however, that jaw form is typically a matter of user preference and surgical application, and that any jaw form, such as straight, curved, tapered, or non-tapered, may be used in conjunction with the present disclosure. The offset electrode arrangement disclosed herein is applicable to any of these forms.

FIGS. 3, 4a, 4b, 5a, and 5b illustrate the distal end of one embodiment of the present invention that provides a highly functional grasper and dissector that can quickly and simply be converted to a scissor by way of finger mechanisms on the handpiece. Included in this embodiment are a grasper device 28 including a lower jaw element 12 having a slot or channel 12A therein, and a upper jaw element 13 having a slot or channel therein 13A, a cutting or scissor device including upper and lower scissor elements (i.e., blades) 14A and 14B, a jaw drive shaft 15, a scissor drive shaft 16, and pivot pins 17a, 17b and 18 for attaching the upper jaw to the lower jaw and the upper scissor element to the lower scissor element respectively. Pivot pins 17a and 17b may be independent components or integral elements of either the upper jaw 13 or lower jaw 12. Likewise, pivot pin 18 may be a separate component or an integral element of either of the scissor blades 14A or 14B. The lower jaw 12 is mounted to shaft 27 that houses the jaw drive shaft 15 and scissor drive shaft 16. The upper jaw is opened by longitudinal distal extension of the jaw drive shaft 15 as indicated by the arrow in FIG. 5a. The scissor blades are driven forward into the jaws by longitudinal distal extension of the blade drive shaft 16 as indicated by the arrow in FIG. 4b. The upper scissor blade insert 14A is pinned to the lower scissor blade insert 14B by pin 18 at a point that permits free pivoting of the upper blade when the scissor blades are deployed into the grasper jaws. The slots in both the upper and lower jaw accommodate the scissor blades when they are deployed, and include a cutting device retaining mechanism (described more fully below) that couples the scissor blades to the respective jaws of the grasping device for pivotal movement therewith. Thus, with the scissor blades deployed, the mechanism that opens and closes the grasper blades can be similarly used to move the scissor blades between similar open and closed positions, allowing them to be used as a scissor.

Figure 4A:
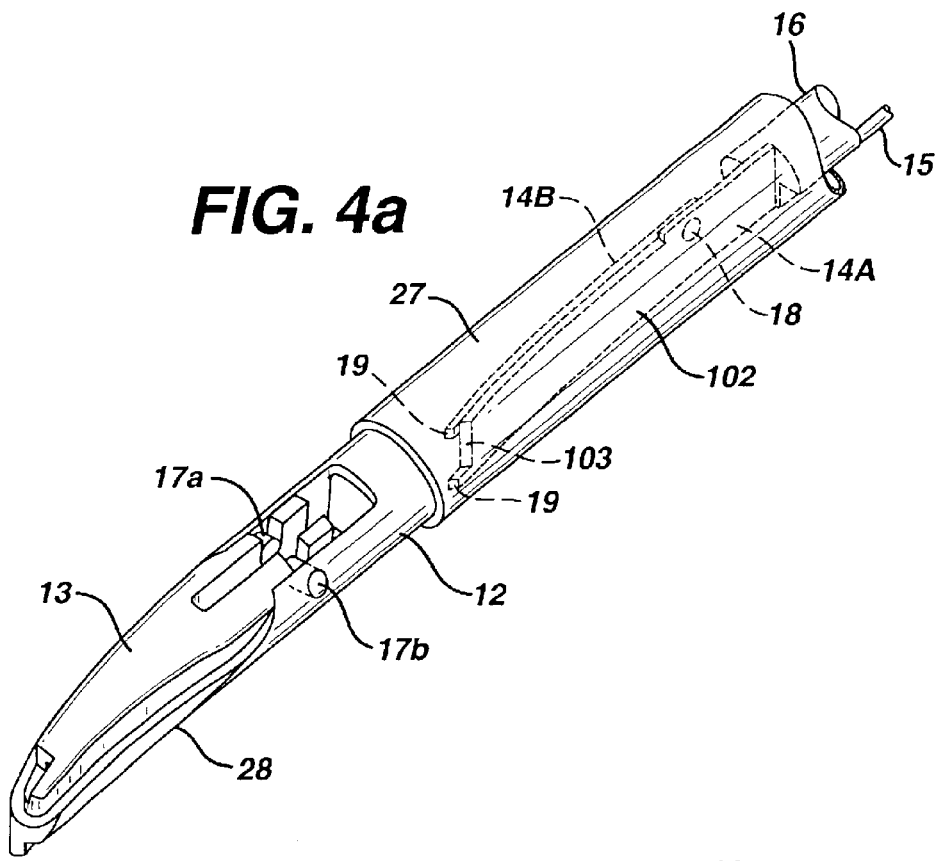
FIG. 4a is an enlarged perspective view of the distal end of the embodiment of FIG. 3 with the grasping device closed and the cutting device retracted.
Figure 4B:
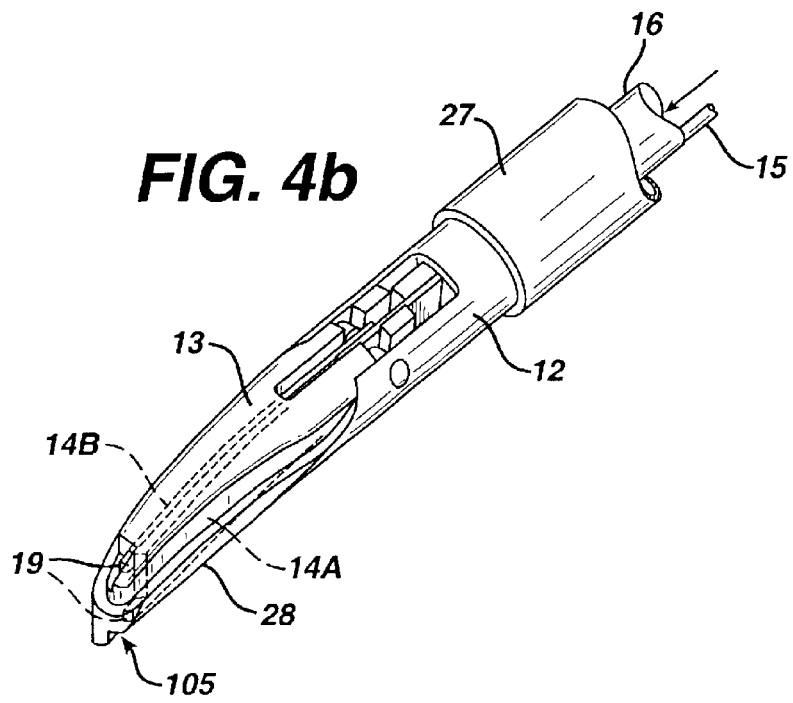
FIG. 4b is an enlarged perspective view of the distal end of the embodiment of FIG. 3 with the grasping device closed and the cutting device deployed.

FIG. 4a shows the distal end of the combination bipolar forcep and scissor surgical instrument where the grasping device 28 is in the closed position, and the scissor device 102 is in the closed position and retracted within the shaft 27. FIG. 4b similarly illustrates both the grasper and scissor devices in the closed position, but with the scissor device in the deployed or extended position where it is positioned within the slots 12A, 13A in the grasper device 28. In this position the scissor device 102 is positioned substantially within the grasper device so that it cannot cut surrounding tissue, but a sharp leading edge 103 of the scissor device may cut any tissue that is being grasped by the grasping device as the scissor device is deployed from the retracted position to the extended position, as will be described in further detail with reference to FIGS. 11a–11d. As indicated above, the scissor device is moved between the retracted position and the extended or deployed position by moving the scissor drive shaft 16 longitudinally forward relative to the outer shaft 27, as shown by the arrow in FIG. 4b.

Figure 5A:
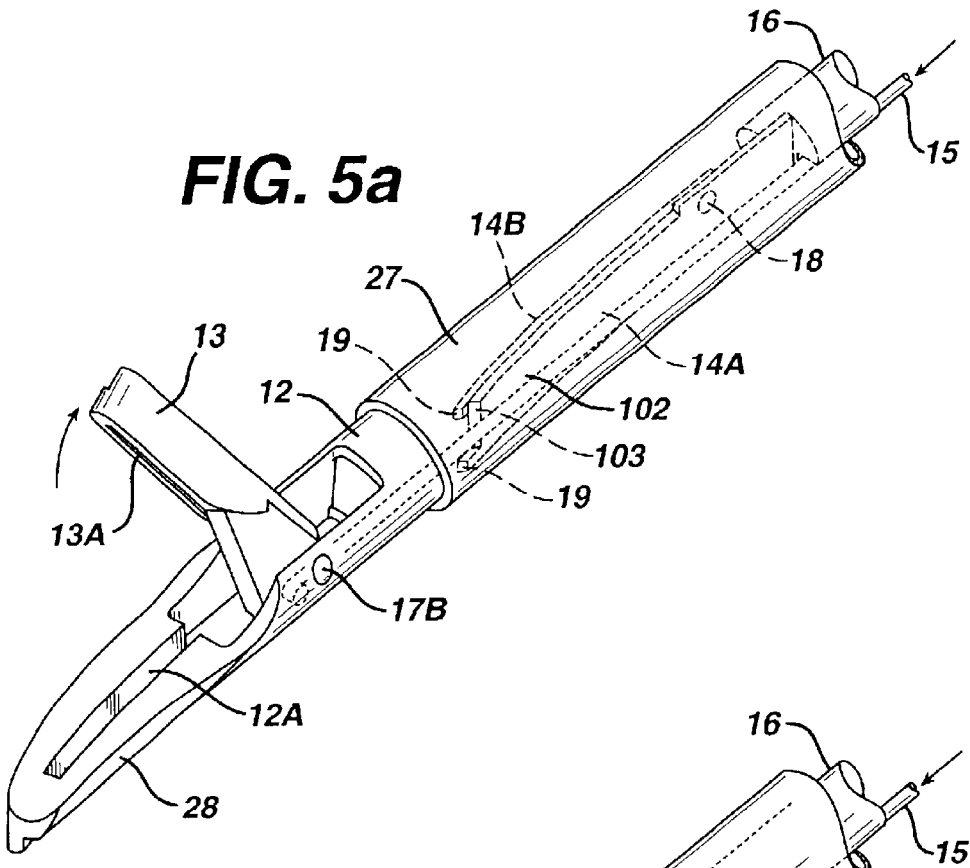
FIG. 5a is an enlarged perspective view of the distal end of the embodiment of FIG. 3 with the grasping device open and the cutting device retracted.
Figure 5B:
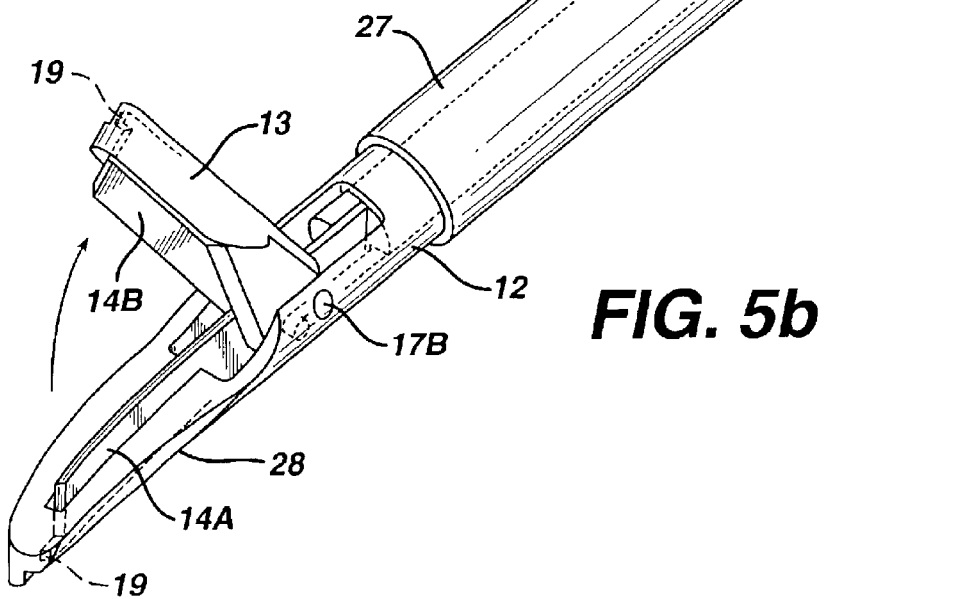
FIG. 5b is an enlarged perspective view of the distal end of the embodiment of FIG. 3 with the grasping device open and the cutting device deployed.
Figure 6A:
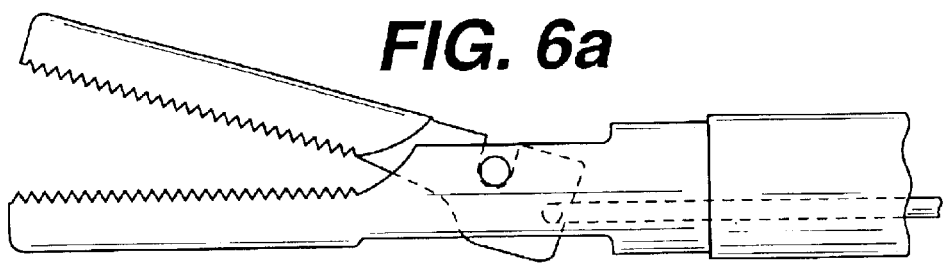
FIGS. 6a–6e illustrate alternate embodiments of the grasping device.
Figure 6B:
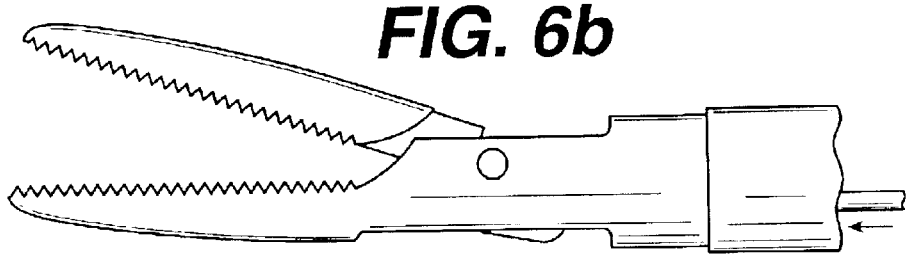
Figure 6C:
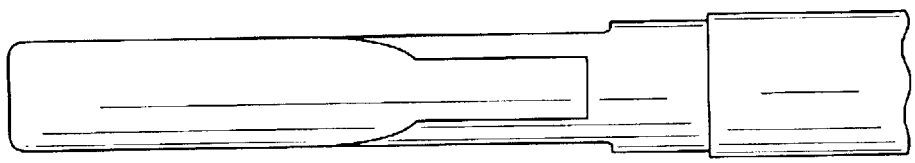
Figure 6D:
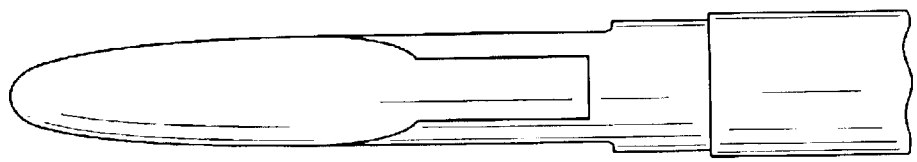
Figure 6E:
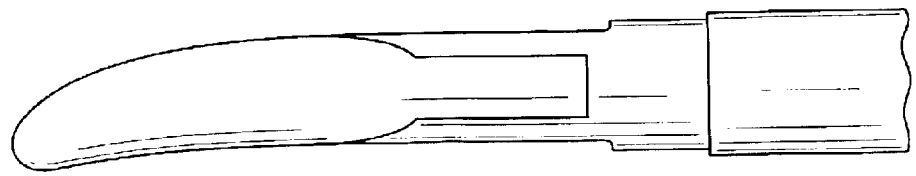

FIG. 5a illustrates the scissor device 102 in the retracted position, and the grasping device 28 in the open position, which is accomplished by moving the jaw drive shaft 15 longitudinally forward relative to the outer shaft 27, as shown by the arrow in FIG. 5a. In this position, the instrument 1 can be used to grasp tissue or the like between the upper and lower jaws 13, 12 of the grasper device 28. Finally, FIG. 5b shows the grasping device in the open position, and the scissor device 102 deployed or extended and also in the open position. In this configuration the instrument 1 can be used as a typical scissor would be.

Figure 13A:
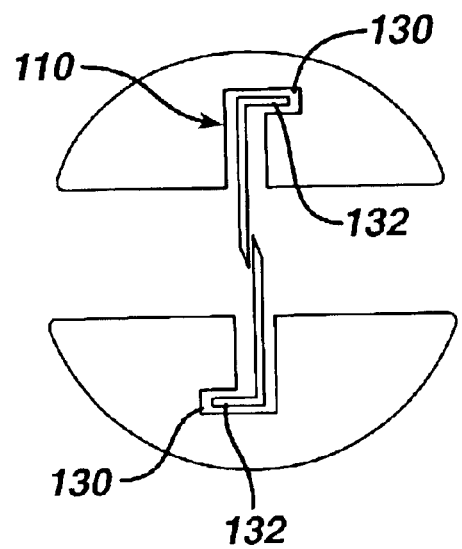
FIGS. 13a and 13b are transverse cross-sectional views of alternate embodiments of the grasping device illustrating possible cutting device retaining mechanisms.
Figure 13B:
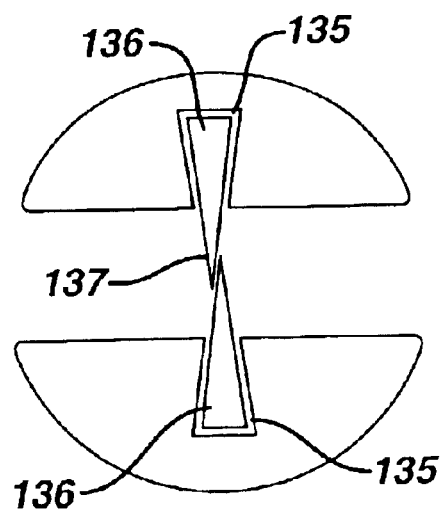

Several different cutting device retaining mechanisms 110 can be used to couple the scissor blades to the jaws when the scissor device is in the deployed position. As illustrated in FIGS. 4a–4b, and 5a–5b the outer sections of the leading edges 103 of both scissor blades 14A, 14B can be equipped with an extension 19 that fits into corresponding holes or cavities in the front regions 105 of the jaws to hold the blades in place. An advantage to this method is that the tapered design of the extension and receptacle cavities will allow the blades to properly mate with the jaws even when the jaws are slightly open or engaging tissue. An alternative method illustrated in FIG. 13a involves using an L-shaped channel 130 on the grasper jaw that captures horizontal ridges 132 on the outer edge of the blade inserts. Yet another method illustrated in FIG. 13b involves a tapered channel 135 in the jaw that is wider at the bottom than the top and employing cutting blade inserts which are similarly formed tapered 136 with wider outer edges tapering to a narrower profile near the shearing surface 137. Those skilled in the art will understand that various other configurations are also possible.

Figure 7A:
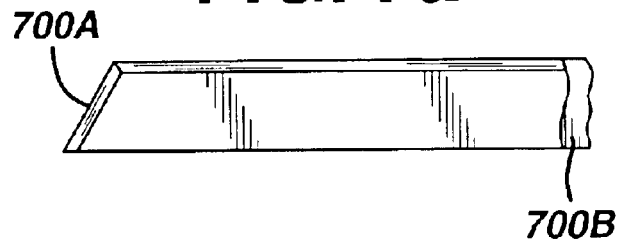
FIGS. 7a–7d are elevational views illustrating other embodiments of the leading edges of the cutting device.
Figure 7B:
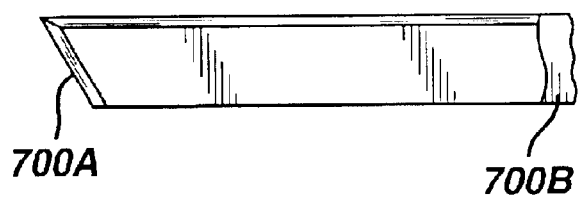
Figure 7C:
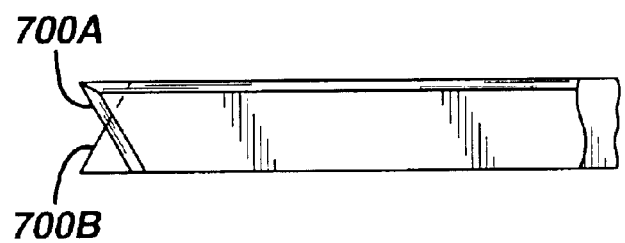
Figure 7D:
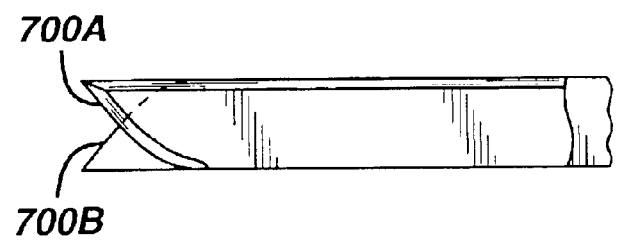

Referring now to FIGS. 7a through 7d, a variety of edge forms and different angles on the leading edges 700A, 700B of the scissor blade inserts may be employed to increase cutting efficacy during blade deployment. Angled blades as illustrated in FIGS. 7a and 7b can increase exposure of the tissue to the blades. In both of these arrangements, the blades may be equal length or one of the blades may be slightly longer, thus reducing the profile of the cutting element and reducing tissue resistance to cutting. Notched arrangements as illustrated in 7c and 7d can also reduce cutting resistance by doubling the cutting edge exposed to the tissue.

Figure 2B:
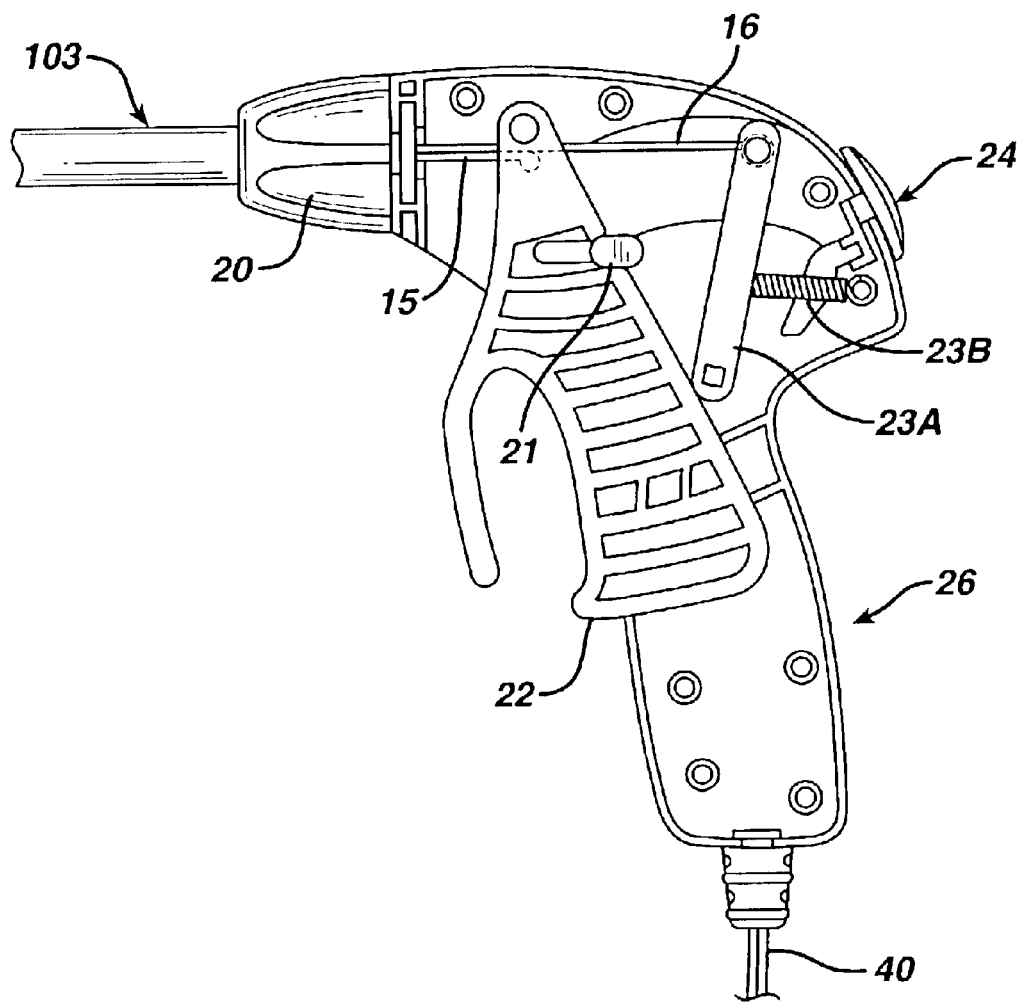
FIG. 2b is a cutaway view of the handle of the device illustrated in FIG. 2a showing the internal mechanisms.

Referring back to FIGS. 2a and 2b, the surgical instrument of the present invention includes a handle 26 coupled to a proximal end 103 of the shaft 27 through which the surgeon manipulates the grasping and/or cutting devices that are positioned at the distal end of the instrument. A rotating knob 20 is directly coupled to both the shaft 27 and the scissor and jaw drive shafts and can be used to rotate the jaw mechanisms to any angle. Mechanisms such as a compression ring in the handpiece associated with this rotating collar can be included to resist unwanted jaw rotation once the trigger mechanism is compressed. Trigger mechanism/finger ring 22 is used to open and close the grasper jaws via direct coupling to the jaw drive shaft. Optimally, this finger ring should accommodate a wide range of hand sizes. Ratchet button 21 enables or disables a jaw ratchet which can be used to lock the position of the jaws relative to each other. When in the active position, teeth in the ratchet button progressively interfere with teeth in the internal portion of the finger ring, preventing reverse motion of the finger ring and associated opening of the jaws. Movement of the ratchet button to the inactive position disengages the ratchet teeth from the teeth in the handle and allows free motion of the finger ring. The cutting mechanism drive lever 23 is coupled to the scissor drive shaft 16 through coupling lever 23A and is used to distend the scissor inserts into slots within the grasper blades. The position of a locking button 24 determines whether the blades will be locked into place upon full extension or return to their resting, stowed position in the instrument shaft after the lever is released. A spring 23B provides tension on the coupling lever 23A which will aid in pulling the scissor mechanism back toward the handle and into its retracted position.

Figure 10A:
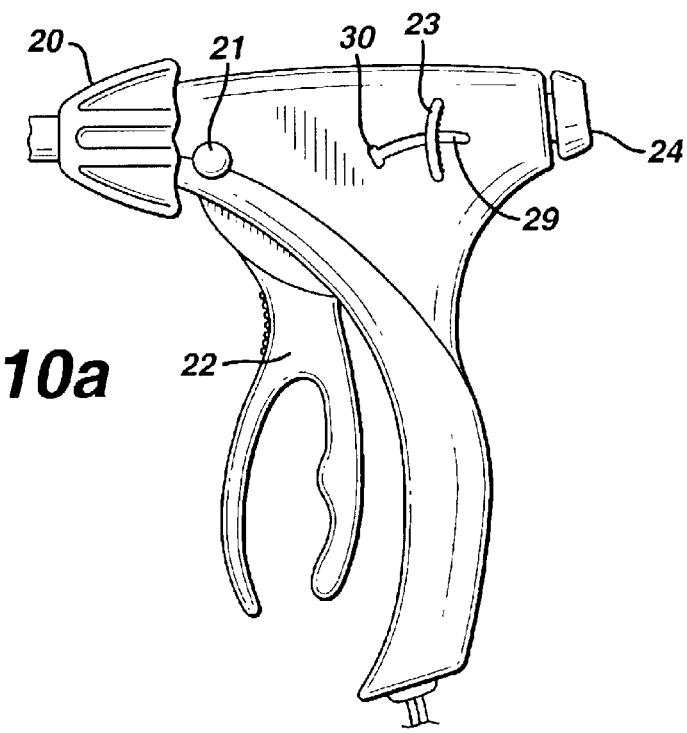
FIGS. 10a–10b are elevational views of various embodiments of a handpiece.
Figure 10B:
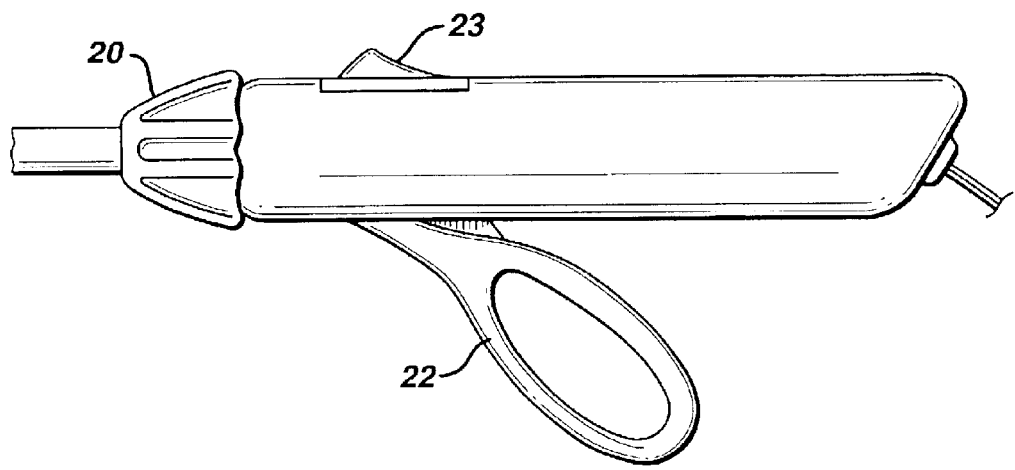

FIG. 10a illustrates an alternate embodiment of the handpiece in which the cutting mechanism drive is accomplished with a sliding button. In this manifestation, locking of the blades in place can be achieved with a detent position at the end of the throw which would allow the blades to be locked in place by an upward or downward manipulation of the lever. FIG. 10b illustrates yet another alternate embodiment of the handpiece in which an in-line/barrel form of handpiece is used. Those skilled in the art will understand that various other configurations of handpieces and control mechanisms are also possible.

Referring again to FIG. 2, exiting the bottom of the handpiece is a bipolar cable 40 suitable for coupling to a bipolar electrosurgical generator 2. In normal application, the users index finger may be employed to adjust the rotary knob 20 and set the ratchet enable/disable button 21. The users thumb may be used to work the cutting mechanism drive lever 23 or slide and set the scissor lock enable disable button 24. The middle, ring, or optionally little fingers may be accommodated by and used to manipulate the trigger mechanism 22.

Figure 11A:
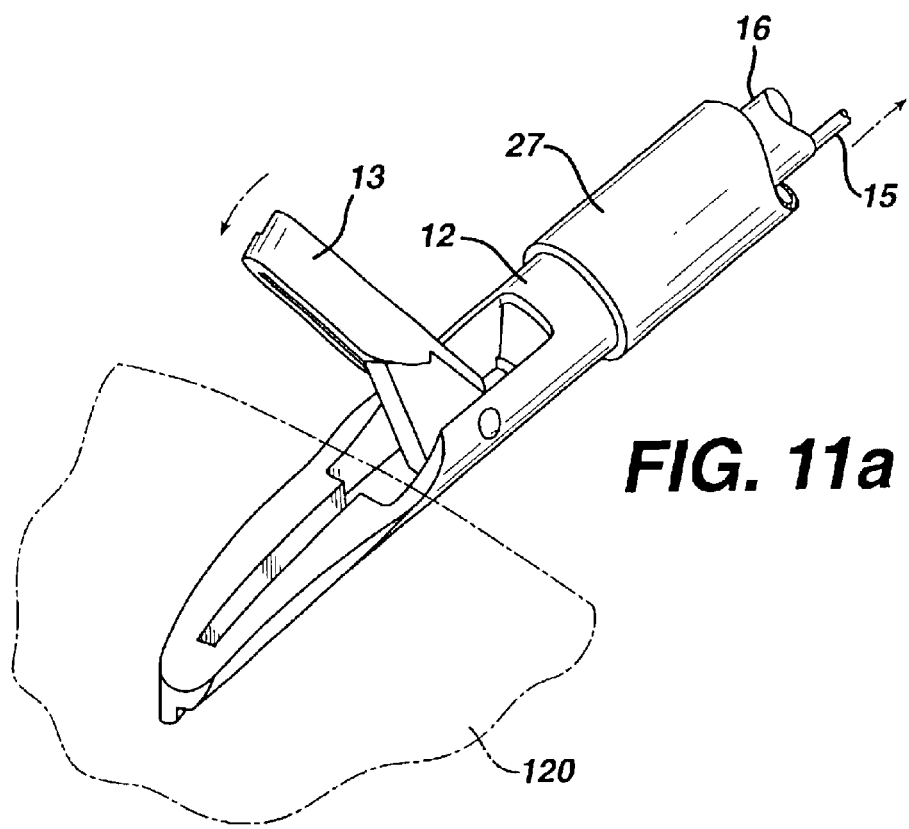

Referring now to FIGS. 11a–11d, and 12a–12d, methods for using the disclosed surgical instrument will now be described in greater detail. According to one method, the grasping device 28 of the surgical instrument is placed in the open position while the cutting device (not shown) is maintained in the retracted position within the shaft 27, as shown in FIG. 11a. Tissue 120 is then grasped by placing the jaws 12, 13 around tissue 120 and subsequently moving the jaws to the closed position shown in FIG. 11b by longitudinally retracting the jaw drive shaft 15, causing the upper jaw 13 to pivot relative to the lower jaw 12 to the closed position. Current is then applied to the bipolar jaws, thereby coagulating the tissue captured between the grasper jaws. Subsequently, the cutting device 102 can be deployed within the grasping device as shown in FIG. 11c to transect the desiccated tissue. The cutting device can once again be retracted and the grasping device opened to remove the instrument from the tissue 120 (FIG. 11d).

Figure 11B:
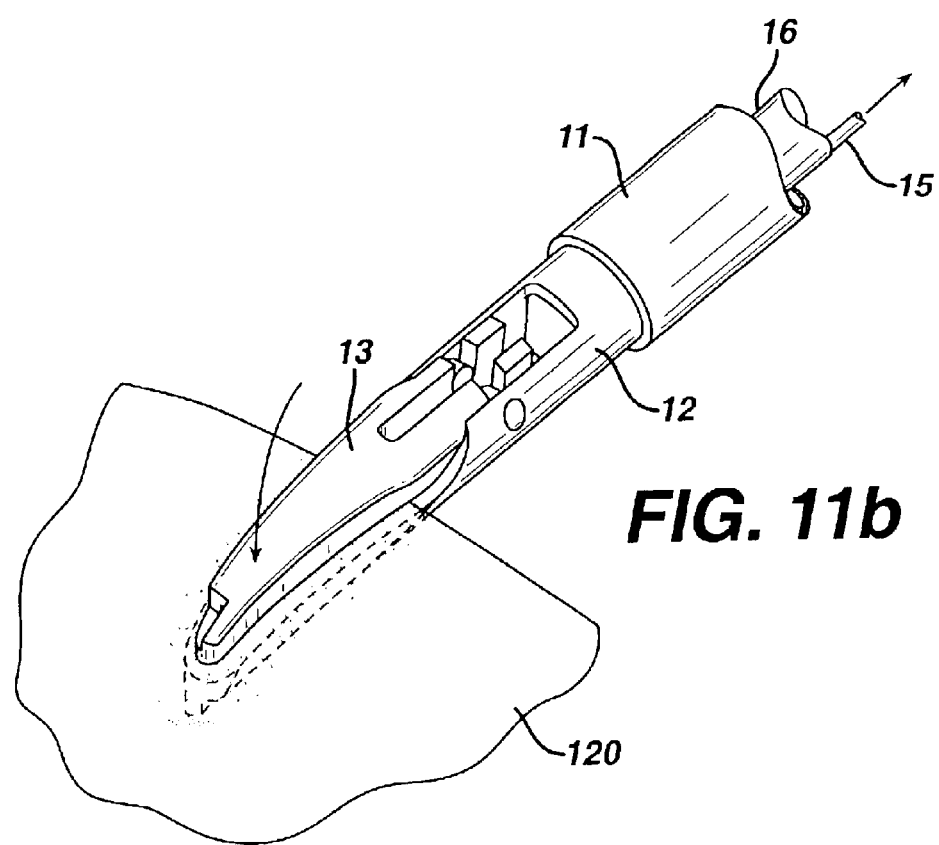
Figure 12A:
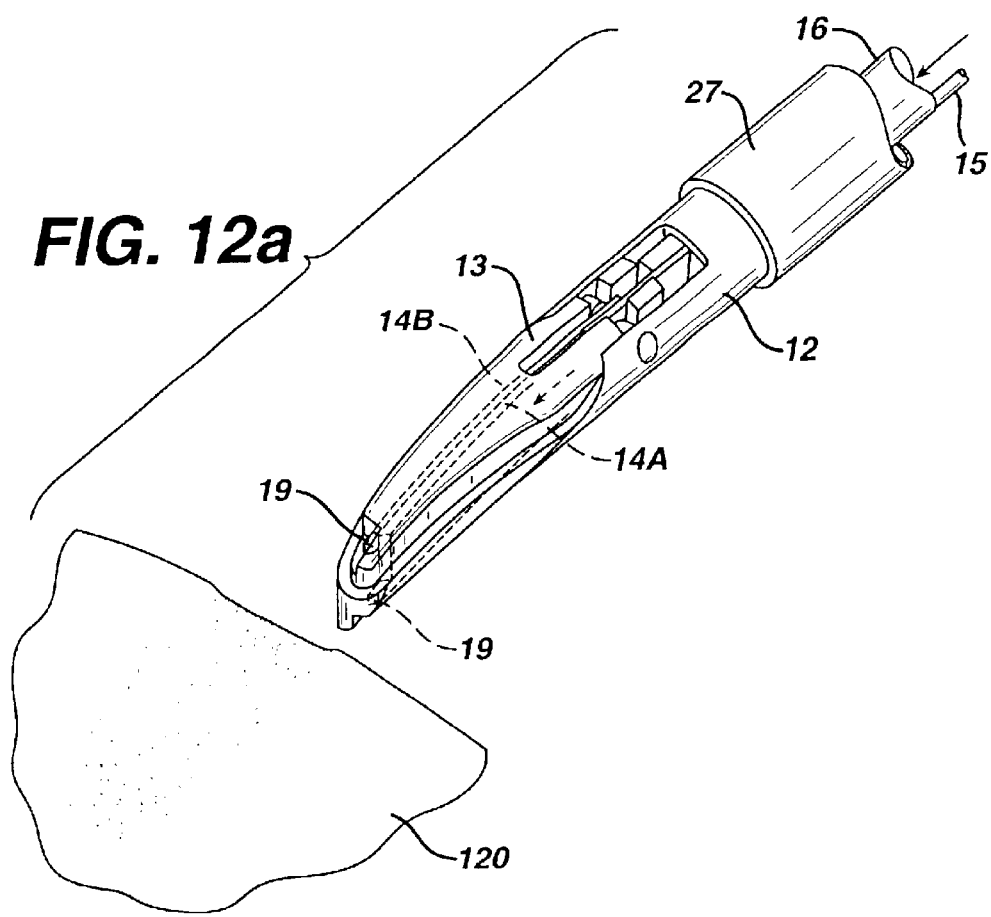
Figure 12B:
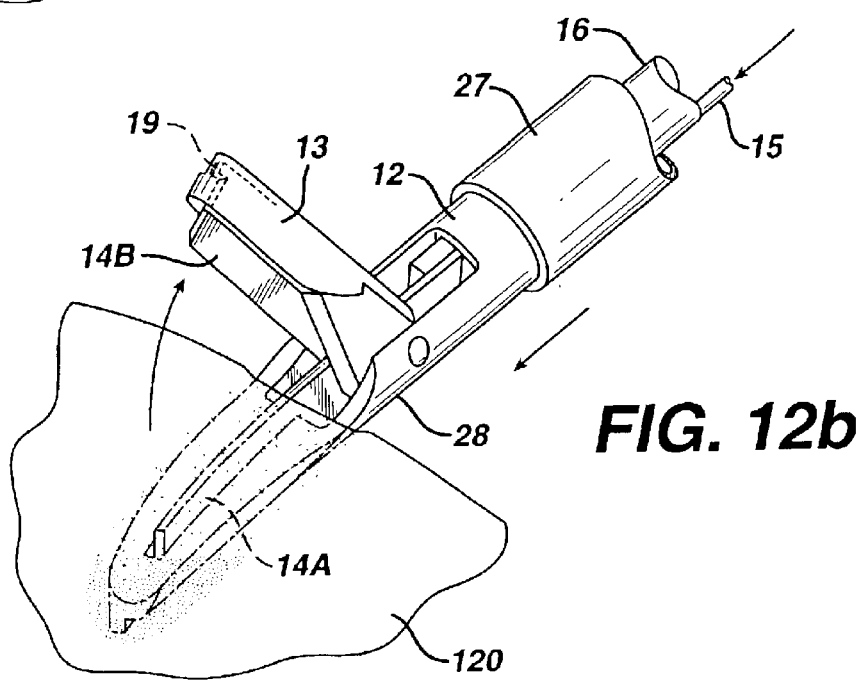

Alternatively, once the tissue has been grasped as shown in FIG. 11b and coagulated, the grasping device can be opened to release the tissue, and re-closed again in order to deploy the cutting device 102 within the grasper device as shown in FIG. 12a. Once the cutting device is deployed, the grasping device is re-opened again, this time in conjunction with the blades of the cutting device as shown in FIG. 12b. The tissue can then be re-grasped, causing cutting of the coagulated tissue by a scissor action, as shown in FIG. 12c. The grasping device is once again opened to finally release the cut tissue (FIG. 12d).

Although exemplary embodiments and methods for use have been described in detail above, those skilled in the art will understand that many variations are possible without departing from the spirit and scope of the invention, which is limited only by the appended claims.

What is claimed is:

1. A surgical instrument comprising:
   a shaft having a proximal end and a distal end;
   a handpiece disposed at the proximal end of the shaft;
   a grasping device disposed at the distal end of the shaft, and having a first jaw element and a second jaw element pivotally coupled to the first jaw element and selectively pivotable relative to the first jaw element between an open jaw position and a closed jaw position; and
   a cutting device having a first cutting element and a second cutting element pivotally coupled to the first cutting element for permitting free unbiased pivoting of the second cutting element relative to the first cutting element, the cutting device being movable between a retracted position wherein it is positioned within the shaft and an extended position wherein it is disposed at the distal end of the shaft, wherein when the cutting device is in the extended position, the second cutting element is retained within the second jaw element to hold the second cutting element in place relative to the second jaw element so that movement of the second jaw element from the open jaw position to the closed jaw position causes a corresponding movement of the second cutting element from an open cutting position to a closed cutting position.

2. The surgical instrument according to claim 1, further comprising:
   a grasper activation assembly for selectively moving the grasping device between the open and closed positions; and
   a cutting device activation assembly for selectively moving the cutting device between the retracted and extended positions.

3. The surgical instrument according to claim 2, wherein the grasping activation assembly further comprises a grasping activator element associated with the handpiece, and grasping activation coupling elements for coupling the grasping activator element with the grasping device so that selective movement of the grasping device between the open and closed positions can be accomplished by manipulating the grasping activator element, and wherein the cutting activation assembly further comprises a cutting activator element associated with the handpiece, and cutting activator coupling elements for coupling the cutting activation element with the cutting device so that selective movement of the cutting device between the retracted and extended positions can be accomplished by manipulating the cutting activator element.

4. The surgical instrument according to claim 3, wherein the grasping activation coupling elements include an elongate element positioned within the shaft, wherein longitudinal movement of the elongate element along the axis of the shaft causes the second jaw element to pivot relative to the first jaw element between the open and closed positions, and wherein the cutting activation elements include an elongate element positioned within the shaft, wherein longitudinal movement of the elongate element along the axis of the shaft causes the cutting device to move between the retracted and extended positions.

5. The surgical instrument according to claim 1, wherein at least one of said first and second cutting elements further comprises a sharpened leading edge.

6. The surgical instrument according to claim 1, further comprising at least one pair of bipolar electrodes contained within the first and second jaw elements respectively, the arrangement being such that when the grasping device is in the closed position, the electrodes are substantially facing towards one another and substantially offset from one another.

7. The surgical instrument according to claim 6, wherein the at least one set of positive and negative electrodes are laterally offset.

8. The surgical instrument according to claim 7, wherein the electrodes are insulated except where exposed at the surface of the first and second jaw elements.

9. The surgical instrument according to claim 1, further comprising at least one pair of bipolar electrodes contained within the first and second jaw elements respectively, the arrangement being such that when the grasping device is in the closed position, the electrodes are substantially facing towards one another and substantially opposing one another.

10. The surgical instrument according to claim 1, further comprising a cutting device safety element that prevents the cutting device from moving from the retracted position to the extended position unless the grasping device is substantially in the closed position.

11. The surgical instrument according to claim 1, wherein the first and second jaw elements have first and second channels therein respectively, and wherein, when in the extended position, the first and second cutting elements are positioned within the first and second channels respectively.

12. The surgical instrument according to claim 1, further comprising means for impeding rotation of the grasping element when in the closed position.

13. The surgical instrument according to claim 1, wherein the first cutting element is retained within the first jaw element when the first cutting element is in the extended position to hold the first cutting element in place relative to the first jaw element.

14. The surgical instrument according to claim 13, wherein the first and second cutting elements have first and second protrusions respectively that, when the cutting device is in the extended position, are retained within first and second recesses in the first and second jaw elements respectively to hold the first and second cutting elements in place relative to the first and second jaw elements.

15. A surgical instrument comprising:
   a shaft having a proximal end and a distal end;
   a handpiece disposed at the proximal end of the shaft;
   a grasping device disposed at the distal end of the shaft having first and second jaw elements pivotally coupled to one another and pivotable relative to one another between an opened jaw position and a closed jaw position; and
   a cutting device having a first cutting element and a second cutting element pivotally coupled to the first cutting element for permitting free unbiased pivoting of the second cutting element relative to the first cutting element, the cutting device being movable between a retracted position wherein it is positioned within the shaft and a extended position wherein it is disposed at the distal end of the shaft, wherein when the cutting device is in the extended position, the second cutting element is retained within the second jaw element to hold the second cutting element in place relative to the second jaw element so that movement of the second jaw element from the opened jaw position to the closed jaw position causes a corresponding movement of the second cutting element from an opened cutting position to a closed cutting position;
   wherein at least one of said first and second cutting elements has a sharpened leading edge capable of dissecting tissue when the cutting device is moved from the retracted position to the extended position.

16. The surgical instrument according to claim 15, further comprising at least one pair of bipolar electrodes contained within the first and second jaw elements respectively, the arrangement of the electrodes being such that when the grasping device is in the closed position the electrodes are substantially facing towards one another and substantially offset from one another.

17. The surgical instrument according to claim 15, further comprising at least one pair of bipolar electrodes contained within the first and second jaw elements respectively, the arrangement of the electrodes being such that when the grasping device is in the closed position the electrodes are substantially facing towards one another and substantially opposing one another.

18. The surgical instrument according to claim 15, further comprising:
   a grasper activation assembly for selectively moving the grasping device between the opened and closed positions, the grasper activation assembly including a grasper activator element associated with the handpiece, and grasper activation coupling elements coupling the grasper activation element to the grasping device, wherein manipulation of the grasper activation element causes movement of the grasping device between the opened and closed positions; and
   a cutting device activation assembly for selectively moving the cutting device between the retracted and extended positions, the cutting device activation assembly including a cutting device activator element associated with the handpiece, and cutting device activation coupling elements coupling the cutting device activator element with the cutting device, wherein manipulation of the cutting device activator element causes movement of the cutting element between the retracted and extended positions.

19. A method for surgically manipulating tissue comprising the steps of:
   grasping a portion of tissue using a grasping device positioned at a distal end of a shaft of a surgical instrument;
   coagulating the grasped tissue by applying bipolar electrical energy to bipolar electrodes within the grasping device;
   deploying a cutting device into the grasping device, the cutting device having a first cutting element and a second cutting element pivotally coupled to the first cutting element for permitting free unbiased pivoting of the second cutting element relative to the first cutting element;
   retaining the deployed cutting device within the grasping device to hold the cutting device in place relative to the grasping device;
   opening the grasping device so as to correspondingly open the cutting device; and
   closing the grasping device around the tissue so as to correspondingly close the cutting device to thereby transect the tissue with the cutting, device.

20. The method according to claim 19, wherein the cutting device has a sharpened leading edge, and the step of deploying the cutting device includes the step of moving the cutting device from a retracted position to an extended position while the grasping device is grasping the tissue so that the sharpened leading edge transects the tissue.

21. The method according to claim 19, wherein the bipolar electrodes within the grasping device are positioned so as to substantially face one another, and are offset from one another.

22. The method according to claim 19, wherein the bipolar electrodes within the grasping device are positioned so as to substantially face one another, and are substantially opposing one another.

* * * * *